(12) United States Patent
Walker et al.

(10) Patent No.: US 7,432,081 B2
(45) Date of Patent: Oct. 7, 2008

(54) EHRLICHIA DISULFIDE BOND FORMATION PROTEINS AND USES THEREOF

(75) Inventors: David H. Walker, Galveston, TX (US); Jere W. McBride, League City, TX (US)

(73) Assignee: Research Development Foundation, Carson City, NV (US)

( * ) Notice: Subject to any disclaimer, the term of this patent is extended or adjusted under 35 U.S.C. 154(b) by 1003 days.

(21) Appl. No.: 10/286,516

(22) Filed: Nov. 1, 2002

(65) Prior Publication Data

US 2003/0092087 A1 May 15, 2003

Related U.S. Application Data

(62) Division of application No. 60/335,611, filed on Nov. 1, 2001.

(51) Int. Cl.
C12P 19/34 (2006.01)
C12P 21/04 (2006.01)
A61K 39/02 (2006.01)

(52) U.S. Cl. .................. 435/91.2; 435/69.7; 435/326; 435/340; 536/23.4; 536/23.7; 424/234.1

(58) Field of Classification Search ............... 435/91.2, 435/69.7, 326, 340; 536/23.4, 23.7; 424/234.1
See application file for complete search history.

(56) References Cited

FOREIGN PATENT DOCUMENTS

| WO | WO-98/16554 | 4/1998 |
|---|---|---|
| WO | WO-99/13720 | 3/1999 |
| WO | WO-00/65063 | 11/2000 |
| WO | WO-02/066652 | 8/2002 |

OTHER PUBLICATIONS

McBride et al , Infection and Immunity, May 2002,vol. 70, No. 5, , p. 2700-2703.*
Missiakas D and Raina S. J Bacteriol. Apr. 1997, 179(8): 2465-71.*
Breitschwerdt et al 1998 (J. Clin. Microbiol 1998 36: 2645-2651).*
Petrovec et al 1997, J. Clin. Microbiol 35: 1556-1559.*
Allsopp et al Journal of Clinical Microbiology, Nov. 2001,vol. 39, 4204-4207.*
Vidotto MC, Infect Immun. Jul. 1994;62(7):2940-6.*
Doyle et al ; Journal of Molecular Diagnostics, vol. 7, No. 4, Oct. 2005.*
Akiyama et al., "In vitro catalysis of oxidative folding of disulfide-bonded proteins by the *Escherichia coli* dsbA (ppfA) gene product," *J. Biol. Chem.*, 267:22440-22445, 1992.
Bardwell et al., "Identification of a protein required for disulfide bond formation in vivo," *Cell*, 67:581-589, 1991.
Isihara et al., "Cloning and characterization of the gene for a protein thiol-disulfide oxidoreductase in *Bacillus brevis*, " *J. Bacteriol.*, 177:745-749,1995.
Liu et al., "Disulfide-dependent folding and export of *Escherichia coli* DsbC," *J. Biol. Chem.*, 276:1146-1151, 2001.
Miranda-Vizuete et al., "Cloning, expression, and characterization of a novel *Escherichia coli* thioredoxin," *J. Biol. Chem.*, 272:30841-30847, 1997.
Missiakas et al., "The *Escherichia coli* dsbC (xprA) gene encodes a periplasmic protein involved in disulfide bond formation," *EMBO J.*, 13:2013-2020, 1994.
Ng et al., "Cloning and expression of the gene for a protein disulfide oxidoreductase from Azotobacter vinelandii: complementation of an *Escherichia coli* dsbA mutant strain," *Gene*, 188:109-113, 1997.
Raina et al., "Making and breaking disulfide bonds," *Annu. Rev. Microbiol.*, 51:179-202, 1997.
Russel et al., "The role of thioredoxin in filamentous phage assembly. Construction, isolation, and characterization of mutant thioredoxins," *J Biol Chem.*, 261:14997-15005, 1986.
Supplementary European Search Report dated Mar. 29, 2006 for European Patent Application No. 02789388.3.

* cited by examiner

*Primary Examiner*—Shanon A. Foley
*Assistant Examiner*—Padma V Baskar
(74) *Attorney, Agent, or Firm*—Fulbright & Jaworski LLP

(57) ABSTRACT

Novel genes encoding homologous immunoreactive thio-disulfide oxidoreductases, or disulfide bond formation (Dsb) proteins from *Ehrlichia chaffeensis* and *Ehrlichia canis* are disclosed. While the *E. chaffeensis* and *E. canis* Dsb proteins are at most only 31% or less homologous to other known Dsb proteins, the *Ehrlichia* Dsbs contain a cysteine active site, Cys-Gly-Tyr-Cys, similar to those in known Dsb proteins. As predicted by 15-amino acid identical N-terminal signal peptides, the proteins are primarily localized in the periplasm of *E. chaffeensis* and *E. canis*, possibly playing a role in antigenicity and pathogenesis. The present invention provides the nucleotide and amino acid sequences and expression vectors for the *E. chaffeensis* and *E. canis* dsb genes, antisera directed against the proteins, and kits to determine whether an individual or animal is infected with a given species of *Ehrlichia*.

8 Claims, 14 Drawing Sheets

Figure 6:
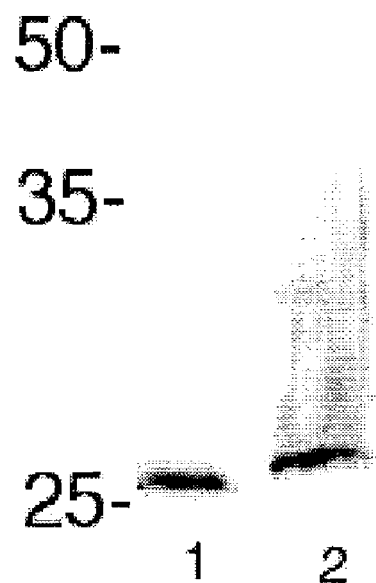

```
ECf dsb  ATGCTAAGGATTTTATTTTTATTAAGTTTAGTTATACTAGTAGCAAGCTTTCCGTTAATA  60
ECa dsb  ATGCTAAGGATT.TATTTTTATTAAG.TTAGT.ATACTAGT.GCAAG.TTTCC..TAATA AACAATTGGTTATCTAGCAAATCTGGTAAAACTATAATAGATAAAGATACAATTATCTCA 120
         AA.AA.TGGTTATCTA..AAATCTGGTAA..CTATA.TAGATAAAGATACAATTAT..CA ATCGTAGAAGAATATATTGCTAATTACCCTCAAAAAGTCATTGACCTCCTAACTAGAGGG 180
         AT..T.GAAGAATATAT..C.AATTACCCTCAAAAAGT.AT.GA.CT.CT.AC.A.AGGG CAAGCACAAGCAGAAAATGAAGAAATGAGTAAAAACATAAAAAAGTATAAATCTGAACTT 240
         CAAG..C..GCAGA.AATGAAGAAATGAGT.AAAACATAAAAAA.TA.AAATCTGAA.T.

GAGGATAGCTCATATCCTTCTGCAGGAAATAAAGACAGTAAAATCGTATTTGTAGAATTC 300
         GA..ATA..TCATATCCTTC.GC.GGAAATAAAGA.AGTAAAAT.GTATTTGTAGA.TTC

TTTGATTACTCTTGTGGTTATTGCAAAATGATGTCTGAAGATATGAAACAAATAATACAA 360
         TTTGATTACTC.TG.GG.TATTGCAAAATGATGTCTGAAGATATGAAACAAATA.TACAA

GATGGTAAAGTACGTGTCATATTTAGAGATTTTCCAATACTTGGAGAAGCATCACTGAAA 420
         GA.GGTAAAGT.C.TGT.ATATT.AGAGATTTTCCAATACTTGG.GA..C.TCACT.AAA
```

Fig. 1A

```
GCTGTTCAAGCAGCAGCACTAGCAGTACACATCTAATAAACCCAAGTAAATACATCGAGTTCTAC  480
G.TG...CAAGCAGCACTAGC.GTACAT.T.AT.AA.CCAA.TAA.TACAT.GA.TTCTA

CATGCTGCACTAAACCATAAGCAGCAATTTAACGATGAATCTATACTAAGTCTAGTCAAA       540
.ATGC.GCACTA.A..A.AAGCA.CA.TTTAA.GATGA.TC.ATA.TAAGT.T..T.AAA

TCAATAGGTATTGCTGAAGAAGATTTTAAAGTTTCATTAGCCAAGAATTCCGACACTATA       600
TCAATAGGTAT..CTGAAGAAGA.TT.AAAGT.TCATTAGC.AA.AAT.C.GA..CTATA

GAAAAAAATGATACAATCTACTAAACATTAACATTAAGCTCAAAAACATTAACATAAGGGCACCCCT  660
GA.AAAAATGATACAATCTAC.A.AGAA.TAGC.CA.AACATTAA.ATAAGGGCAC.CCT

CGCATTATATAATAGGAGATACATTTATTGGTGGAGCAGCTGATATATCTACTTTAAGAAGT    720
GC.AT.ATA.TAGG.GATACATTTAT.GGTGG.GCAGCTGATATATC.ACTTTAAGAAGT

AAAATAGATGAGCAAGGA    (SEQ ID NO: 2)                              738
AAAATAGAT..GCA...A   (SEQ ID NO: 3)
```

Fig. 1B

```
ECF dsb  M--LRILFLLSLVILVASFFPLINNWLSSKS                                    28
ECf dsb  M--LRILFLLSLVILVASFFPLINNWLSKS                                     28
Com1     ·········L·FL·L···L·A········INN·L··S·                             26

ECF dsb  GKTHIDKDTHIEEYIANYPQKVID----L                                      56
ECf dsb  GK-HID-KDTHIEEY---NYPQKVID--L                                      56
Com1     ········T·······Y····N·P··V·ID····                                 57

ECF dsb  LTRGQAQAENEEMSKNIKKYKSEL-EDSSYP                                    86
ECf dsb  LT-GQ·AENEEMSKNIKKYKSEL-EDS·YP                                     86
Com1     L··········EMS····IK······L··D·····P                               88

ECF dsb  SAGNKDSKIVFFVEFFDYSCGYCKMMSEDMKQ                                   117
ECf dsb  SAGNKDSKIVFFVEFFDYSCGYCKMMSEDMKQ                                   117
Com1     A···········V····DY··CG·CKM·······                                 119
```

Fig. 2A

```
                                            147                178                209                234           246
                                            147                178                209                234           246
                                            150                179                208                239           252

H Q D G K I V R F I D F P H L G E A S L K A V Q A A L A    V H L N P S K Y F Y H A A L N H K Q Q F N D E S I L S L    V K S I G A E E D F K K V S L A K N S D T H E K M I Q S T K E    L A Q N I H R G T P A H I - - - - - - - T F H H I G G A A D    I S T L R S K I D - Q G H I H D F P I L G E A S L K A
H Q D G K I V R F I D F P H L G E A S L K A A       V H L N P S K Y F Y H A A L N H K Q Q F N D E S I L S      K S I G A E E D F K K V S L A K N S D T H E K M I Q S T    L A Q N I H R G T P A H I - - - - - - - T F H H I G G A A D    I S T L R S K I D - Q
I H   K   R V     F   P I L G   S L K   A A L A          V   I H   S K Y F Y H A A L   Q Q   I L S L    V       G         K   L A K       I   M I Q    T .       A   I H - G T P A - - - - - - - - F H I G A . A    I H L R S K . . . .

(SEQ ID NO: 4)
                                                                    (SEQ ID NO: 5)
                                                                    (SEQ ID NO: 6)
```

Fig. 2B

| | | |
|---|---|---|
| Ehrlichia Dsb | Cys-Gly-Tyr-Cys | (SEQ ID NO. 7) |
| C. burnetii Com1 | Cys-Gly-His-Cys | (SEQ ID NO. 8) |
| E. coli DsbA | Cys-Pro-His-Cys | (SEQ ID NO. 9) |
| E. coli DsbC | Cys-Gly-Tyr-Cys | (SEQ ID NO. 10) |
| E. coli thioredoxin | Cys-Gly-Pro-Cys | (SEQ ID NO. 11) |
| PDI (rat) | Cys-Gly-His-Cys | (SEQ ID NO. 20) |

Fig. 3

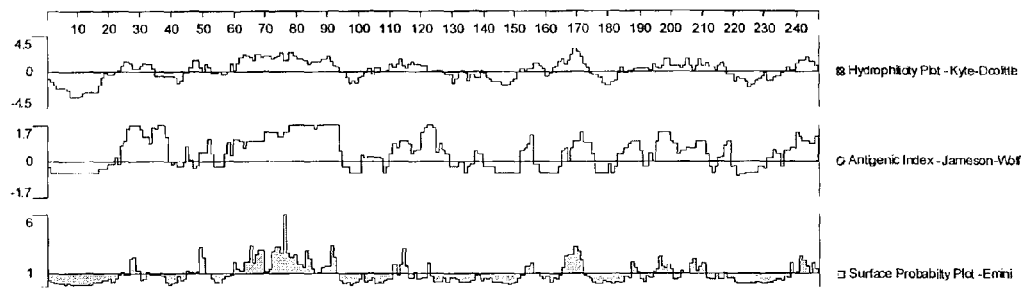
*E. chaffeensis* Dsb
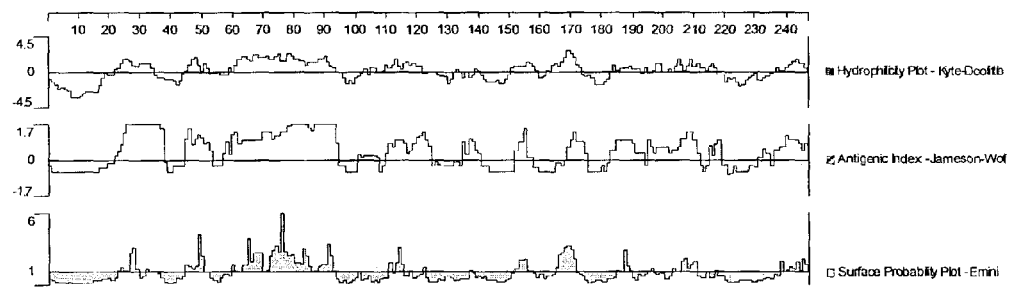
*E. canis* Dsb
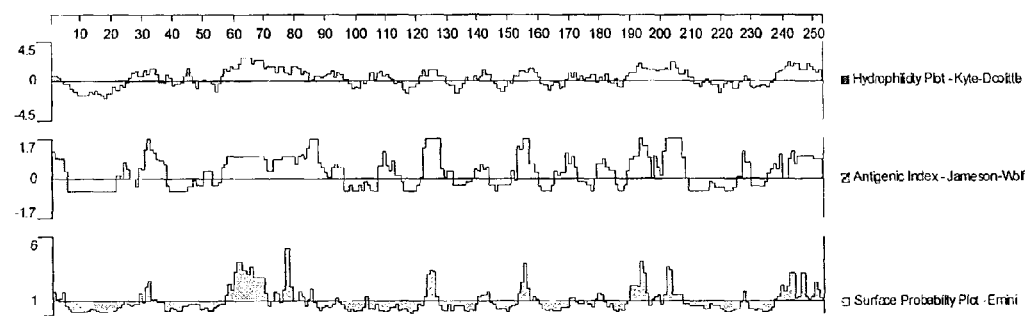
*C. burnetti* Com1
Fig. 4A

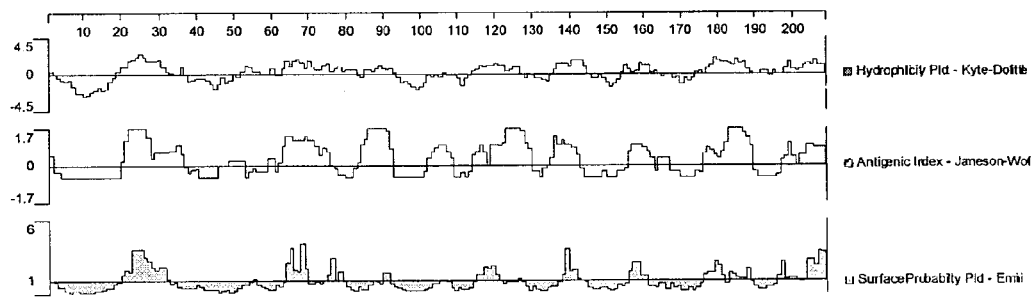
*E. coli* DsbA
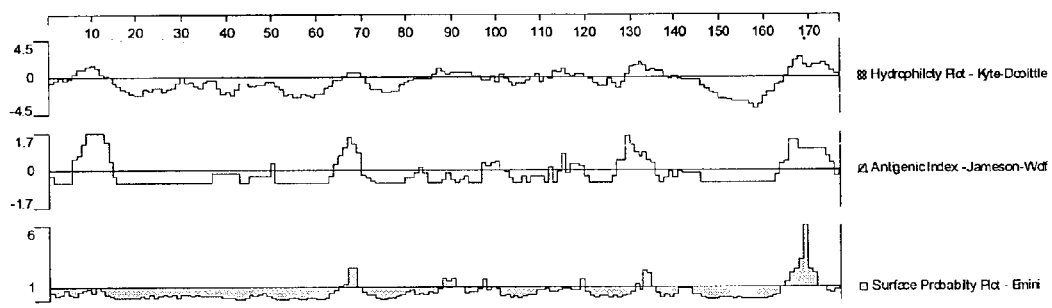
*E. coli* DsbB
Fig. 4B

Fig. 5A    Fig. 5B    Fig. 5C

*EHRLICHIA* DISULFIDE BOND FORMATION PROTEINS AND USES THEREOF

CROSS-REFERENCE TO RELATED APPLICATION

This non-provisional patent application claims benefit of provisional patent application No. 60/335,611, filed Nov. 1, 2001, now abandoned.

FEDERAL FUNDING LEGEND

This invention was produced in part using funds from the Federal government under grant no. AI31431 from the National Institute of Allergy and Infectious Diseases. Accordingly, the Federal government has certain rights in this invention.

BACKGROUND OF THE INVENTION

1. Field of the Invention

The present invention relates generally to the fields of bacterial genetics, immunology and microbial pathogenesis. More specifically, the instant invention relates to disulfide bond formation, gram-negative cell envelope structure, and protein folding and assembly in bacteria of the genus *Ehrlichia*. Most specifically, the present invention relates to genes encoding thio-disulfide oxidoreductases, also known as disulfide bond formation (Dsb) proteins, from *Ehrlichia chaffeensis* and *Ehrlichia canis*.

2. Description of the Related Art

The gram-negative bacterial cell envelope consists of proteins, lipoproteins, carbohydrates and peptidoglycan, which interact to form a complex supramolecular structure. While organisms in the genus *Ehrlichia* have typical gram-negative cell envelope structures, limited ultrastructural studies suggest that peptidoglycan is not present. In the absence of peptidoglycan, the structure of gram-negative bacterial outer membranes may be more dependent on covalent and noncovalent associations between outer membrane proteins. Disulfide bond linkages between cell envelope proteins in *Ehrlichiae* have not been determined. However, covalent disulfide bonds between major surface proteins (MSPs) have been observed in the related organism *Anaplasma marginale*, indicating that disulfide linkages are important in the outer membrane structure (18).

Two ultrastructural forms of *Ehrlichia chaffeensis*, termed reticulate and dense-cored cells, correspond to ultrastructurally similar reticulate and elementary body forms observed in *Chlamydiae* (15). Little is known regarding the mechanism(s) of the outer membrane supramolecular rearrangements leading to these ultrastructurally defined forms, but an increase in disulfide crosslinked proteins has been described in elementary bodies of *Chlamydia* spp. (3). The similarity in ultrastructural forms between these two organisms indicates that disulfide bonds may be involved in cell envelope changes leading to the formation of dense-cored cells.

Thio-disulfide oxidoreductases have been characterized in the cell envelopes of several bacteria (1,5,12); these enzymes are likely to be involved in determining the three-dimensional structure of folded outer membrane proteins by catalyzing intra- and intermolecular disulfide bond formation. Although there is little overall sequence homology among disulfide bond formation proteins from various bacteria, certain features are shared, including a conserved cysteine motif (CXXC) (SEQ ID No. 1) that serves as the active site, a thioredoxin domain consisting of a secondary protein fold, and a protein reductant or oxidant activity (10,16). Such proteins have been grouped into the thioredoxin superfamily.

Disulfide oxidoreductases in *Escherichia coli* include thioredoxin and disulfide bond formation (Dsb) proteins A, B, C, D and E (10,16,17). DsbA and DsbB of *E. coli* were recognized by screening mutants that were defective in alkaline phosphatase (AP) activity, protein insertion, and sensitivity to the reducing agent dithiothreitol (DTT) (1,6,8). Other suppressors of dithiothreitol susceptibility were later identified as DsbC, D and E, enzymes that have disulfide isomerase or reductase activities (9,11). Some overlap in function occurs among these disulfide bond formation proteins, as shown by the fact that overexpression of DsbC can alleviate the defects in DsbA mutants (9).

The prior art is deficient in knowledge about the thio-disulfide oxidoreductases or disulfide bond formation proteins present in *E. chaffeensis* and *E. canis*. The present invention fulfills this longstanding need and desire in the art.

SUMMARY OF THE INVENTION

The instant invention encompasses the identification and functional characterization of genes encoding homologous thio-disulfide oxidoreductases of *E. chaffeensis* and *E. canis*. These proteins may be involved in the development of outer membrane supramolecular structures leading to ultrastructural changes in the cell envelope, and folding and assembly of proteins involved in virulence. These changes may play a role in pathogenesis by the *Ehrlichia* genus.

One embodiment of the instant invention provides DNA encoding disulfide bond formation (Dsb) proteins from bacterial species of the genus *Ehrlichia*, such as *Ehrlichia chaffeensis* and *Ehrlichia canis* disulfide bond formation proteins.

In another embodiment of the instant invention, expression vectors encoding disulfide bond formation proteins and regulatory elements necessary for expression of the DNA in a cell are provided. These vectors may be used to express the proteins in mammalian cells, plant cells, insect cells or bacterial cells such as *E. coli*.

A further embodiment of the instant invention provides isolated and purified disulfide bond formation proteins from *Ehrlichia*. Preferably, these proteins have thio-disulfide oxidoreductase enzymatic activity and are isolated from either *Ehrlichia chaffeensis* or *Ehrlichia canis*.

In yet another embodiment of the invention, antibodies against specific *Ehrlichia* disulfide bond formation proteins are described. These antibodies may comprise either monoclonal antibodies or polyclonal antisera.

Another embodiment of the instant invention include the use of *Ehrlichia* disulfide bond formation proteins as modifiers utilized in in vitro translation to catalyze disulfide bonds in proteins in which such bonds contribute to the proper folding, conformation and potential functional activity.

Additional embodiments of the instant invention include methods of determining whether an animal or individual has been infected with a given species of *Ehrlichia*. These methods may be accomplished by determining whether serum from said animal or individual reacts with a disulfide bond formation protein from a specific species of *Ehrlichia* or by PCR amplification of a dsb gene encoding a disulfide bond formation protein specific to an individual species of *Ehrlichia*. Kits for either method are provided to facilitate application of these methods to a clinical setting.

Additional embodiments of the instant invention include vaccines against individual species of the *Ehrlichia* genus consisting of bacteria attenuated by inactivation of the dsb gene. Such vaccines include a vaccine against *Ehrlichia chaf-* feensis to prevent or treat human monocytotropic ehrlichiosis (HME) and a vaccine against *Ehrlichia canis* to prevent or treat canine monocytic ehrlichiosis (CME).

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A and FIG. 1B show the nucleic acid sequence alignment of the 738-bp *E. chaffeensis* (ECf disulfide bond formation) gene (SEQ ID No. 2) and the *E. canis* dsb (ECa disulfide bond formation) gene (SEQ ID No. 3). Nucleotides divergent from *E. chaffeensis* dsb are designated by a dot.

FIG. 2A and FIG. 2B show sequence alignments of the 246 amino acid disulfide bond formation proteins of *E. chaffeensis* (SEQ ID No. 4) and *E. canis*, (SEQ ID No. 5), and the 252 amino acid *C. burnetii* Com1 (SEQ ID No. 6). The *Ehrlichia* proteins were 87% homologous to each other and 31% homologous to *C. burnetii* Com1. The 15 amino acid leader sequences and the cysteine active sites are boxed. Gaps introduced for maximal alignment are designated with a dash. Amino acids divergent from *E. chaffeensis* Dsb are designated by a dot.

FIG. 3 shows a comparison of the catalytic active sites of other reported disulfide oxidoreductases with those of the *Ehrlichia* Dsb proteins. The *Ehrlichia* disulfide bond formation cysteine active site is found at amino acids 105-108.

FIG. 4A and FIG. 4B show a comparison of predicted protein characteristics of *E. coli* DsbA (periplasmic), *E. coli* DsbB (cytoplasmic membrane), *E. chaffeensis* and *E. canis* disulfide bond formation proteins, and *C. burnetii* Com1 using Kyte-Doolittle hydropathy, Jameson-Wolf antigenic index, and Emini surface probability plots. The hydrophilicity plots predict regional hydropathy based on amino acid sequences derived from water vapor transfer free energies and interior and exterior distribution of residue side chains. The antigenic index predicts potential antigenic determinants. The regions with values above zero are potential antigenic determinants. Surface probability predicts the surface residues by using a window of hexapeptides. A surface residue is any residue with >2.0 $nm^2$ of water-accessible surface area. A hexapeptide value higher than 1 was considered a surface region.

Figures 5A, 5B, 5C:
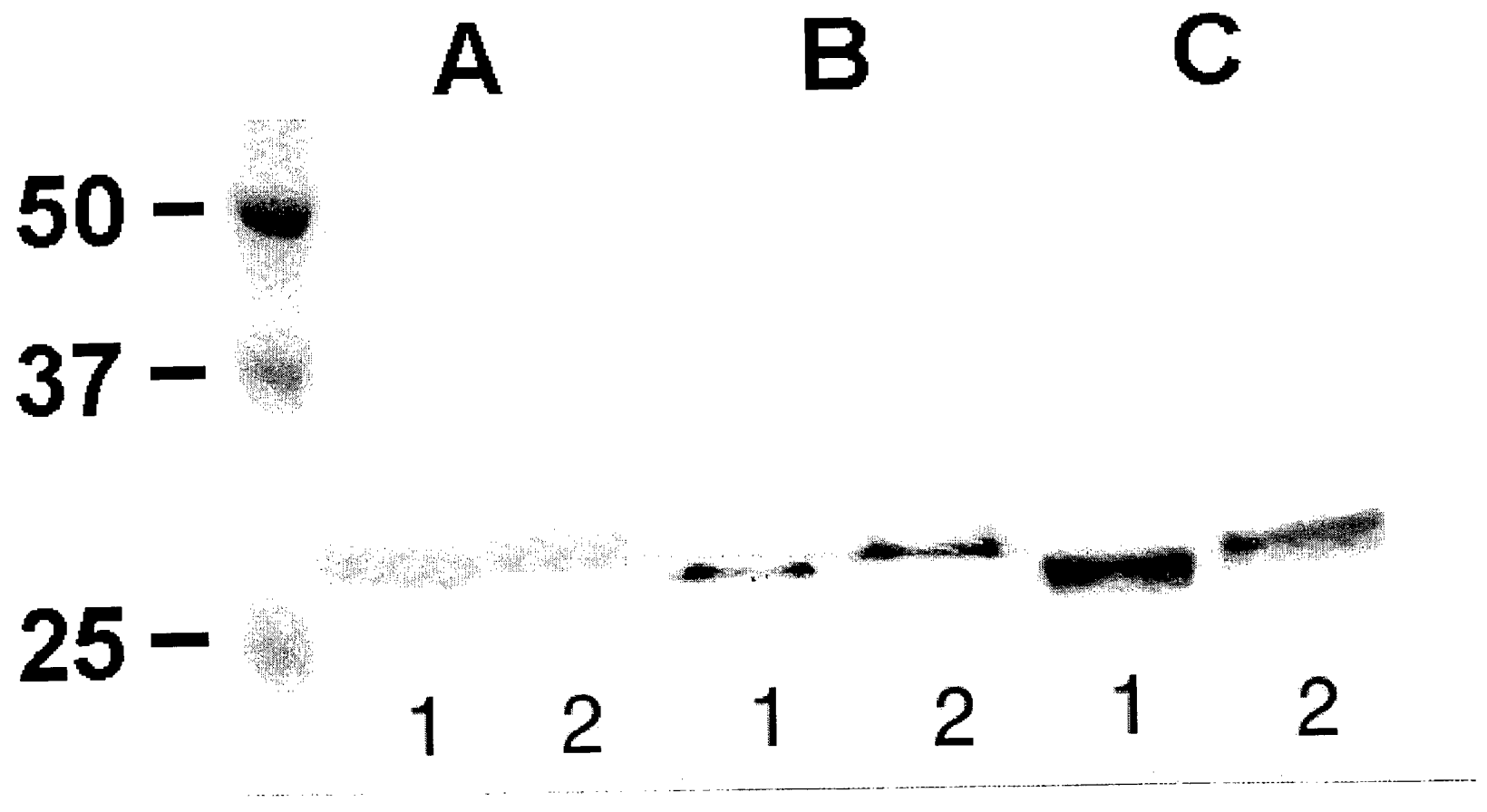

FIG. 5A shows SDS-PAGE of *E. canis* (lane 1) and *E. chaffeensis* (lane 2) partial rDsb proteins (−25 N-terminal amino acids) expressed in *E. coli*. The C-terminal polyhistidine fusion tag accounts for approximately 5 kDa of the molecular mass. Corresponding Western blots using *E. canis* anti-rDsb (FIG. 5B) and *E. chaffeensis* anti-rdsb (FIG. 5C) demonstrate homologous and heterologous immune reactivity of the *Ehrlichia* disulfide bond formation proteins.

FIG. 6 shows an immunoblot of SDS-PAGE separated *E. canis* (lane 1) and *E. chaffeensis* (lane 2) whole cell lysates reacted with *E. chaffeensis* anti-rdsb. The anti-rdsb antibody reacted with native proteins in both *E. canis* (26 kDa) and *E. chaffeensis* (27 kDa) with a similar size to the rDsb.

FIGS. 7A-7C show immunoblots of HME patient sera (13) reacted with *E. chaffeensis* rDsb (FIG. 7A) and canine monocytic ehrlichiosis dog sera (13) reacted with *E. chaffeensis* rdsb (FIG. 7B) and *E. canis* rDsb (FIG. 7C). The human monocytotropic ehrlichiosis patient sera were nonreactive with the *E. chaffeensis* rDsb, but the canine monocytic ehrlichiosis dog sera reacted with the *E. canis* rdsb and cross-reacted with the *E. chaffeensis* rDsb.

FIGS. 8A-8D show complementation of the *E. coli* dsbA mutant JCB572 by the *E. chaffeensis* dsb gene. Motility was observed on LB soft agar plates for the reference strain *E. coli* JCM502 (FIG. 8A) and *E. coli* JCB572 [pECf-Dsb] (FIG. 8B). Motility was not observed for *E. chaffeensis* dsb signal peptide deficient complementation *E. coli* JCB572 [pECf-Dsb-sp] (FIG. 8C), and control plasmid, *E. coli* JCB572 [placZ] (FIG. 8D).

FIG. 9 shows alkaline phosphatase activity of complemented *E. coli* dsbA mutants, including the *E. coli* JCM502 positive control strain (1), *E. chaffeensis* dsb complemented *E. coli* JCB572 [pECf-Dsb], *E. chaffeensis* dsb N-terminal deficient complemented *E. coli* JCB572 [pECf-Dsb-sp], and the plasmid control, *E. coli* JCB572 [placZ] (pCTRL).

FIGS. 10A and 10B shows post embedding immuno-gold staining of *E. chaffeensis* and *E. canis* with antibodies against *E. chaffeensis* rDsb. Bar=1 μm. FIG. 10A is of *E. chaffeensis* (Arkansas strain) in DH82 cells, while FIG. 10B shows *E. canis* (Oklahoma strain) in DH82 cells. The label is principally localized in the periplasmic space (arrows), as well as in the cytoplasm and at the surface of both organisms.

DETAILED DESCRIPTION OF THE INVENTION

In the instant invention, the genes encoding homologous immunoreactive thio-disulfide oxidoreductases or disulfide bond formation (Dsb) proteins of *Ehrlichia chaffeensis* and *Ehrlichia* can is were identified, cloned and functionally tested. Nucleic acid sequence homology was not observed between the *Ehrlichia* dsb genes and those reported in other bacteria. A conserved amino acid domain architecture was identified in the *Ehrlichia* disulfide bond formation proteins, which was most similar to *Escherichia coli* DsbA and was conserved among members of the thioredoxin superfamily. A cysteine active site, Cys-Gly-Tyr-Cys (SEQ ID No. 7), identical to that of *E. coli* DsbC, is present in the *Ehrlichia* Dsb proteins. The *E. chaffeensis* and *E. canis* disulfide bond formation proteins were 87% homologous, had predicted molecular masses of 27.5 and 27.7 kDa, respectively, and had some homology (31%) to *Coxiella burnetii* Com1. Identical predicted 15 amino acid N-terminal signal sequences were identified in the *Ehrlichia* Dsb proteins, suggesting that they are post-translationally modified and transported extracytoplasmically.

Complementation of an *E. coli* dsbA mutant with *E. chaffeensis* dsb resulted in the restoration of disulfide bonding formation activity, as evidenced by motility and alkaline phosphatase (AP) activity; but *E. chaffeensis* dsb lacking the signal sequence region did not restore motility, and exhibited reduced alkaline phosphatase activity. Antisera from *E. chaffeensis*-infected patients did not react with the *E. chaffeensis* recombinant Dsb (rDsb), but sera from *E. canis*-infected dogs reacted strongly with the *E. canis* rDsb and cross-reacted with the *E. chaffeensis* rDsb. Antisera raised against the respective recombinant proteins were cross-reactive and recognized native *E. chaffeensis* (26 kDa) and *E. canis* (25 kDa) proteins in whole cell lysates. The *Ehrlichia* Dsb proteins were observed primarily in the periplasm of *E. chaffeensis* and *E. canis*.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes". [IRL Press, (1986)];. B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acids described herein are preferred to be in the "L" isomeric form. However, residues in the "D" isomeric form can be substituted for any L-amino acid residue, as long as the desired functional property of immunoglobulin binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage or cosmid, to which another DNA segment may be attached so as to bring about the replication of the attached segment.

A "DNA molecule" refers to the polymeric form of deoxyribonucleotides (adenine, guanine, thymine, or cytosine), in either its single stranded form, or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. Discussion of DNA structure herein is according to the normal convention of giving the sequence only in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence to hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally occurring mutational events do not give rise to a heterologous region of DNA as defined herein.

The labels most commonly employed for these studies are radioactive elements, enzymes, chemicals that fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes that can be used in these procedures are known and can be utilized. The preferred enzymes are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling materials and methods.

A particular assay system developed and utilized in the art is known as a receptor assay. In a receptor assay, the material to be assayed is appropriately labeled. Certain cellular test colonies are then inoculated with a quantity of the labeled material, after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene that encodes a protein of the present invention can be used to transform a host using any of the techniques commonly known to those of ordinary skill in the art. Prokaryotic hosts may include *E. coli, S. typhimurium, Serratia marcescens* and *Bacillus subtilis*. Eukaryotic hosts include yeasts such as *Pichia pastoris*, mammalian cells and insect cells.

In general, expression vectors containing promoter sequences that facilitate the efficient transcription of the inserted DNA fragment are used in connection with the host. The expression vector typically contains an origin of replication, promoter(s), terminator(s), as well as specific genes that are capable of providing phenotypic selection in transformed cells. The transformed hosts can be fermented and cultured according to means known in the art to achieve optimal cell growth.

Methods that are well known to those skilled in the art can be used to construct expression vectors containing appropriate transcriptional and translational control signals. See, for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

The current invention is directed to isolated DNA encoding a disulfide bond formation (Dsb) protein from bacteria of the genus *Ehrlichia*, said DNA selected from the group consisting of:
(a) isolated DNA which encodes an *Ehrlichia* disulfide bond formation protein; (b) isolated DNA which hybridizes to the isolated DNA of (a) above under high stringency conditions consisting of hybridization at 42° C. in the presence of about 50% formamide, a first wash at 65° C. with 2×SSC containing 1% SDS, and a second wash at 65° C. with 0.1×SSC, and which encodes a disulfide bond formation protein; and, (c) isolated DNA differing from the isolated DNAs of (a) and (b) above in codon sequence due to the degeneracy of the genetic code, and which encodes an *Ehrlichia* disulfide bond formation protein. The DNA may encode a disulfide bond formation protein from *Ehrlichia chaffeensis*, which may have the nucleotide sequence shown in SEQ ID No: 2 encoding a protein of amino acid sequence SEQ ID No: 4. Alternatively, the DNA may encode an *Ehrlichia canis* disulfide bond formation protein and may possibly consist of DNA of nucleotide sequence SEQ ID No: 3, encoding a protein of amino acid sequence SEQ ID No: 5.

The instant invention also provides expression vectors encoding disulfide bond formation proteins and regulatory elements necessary for expression of the DNA in a cell. The vector may be used to express the proteins in mammalian cells, plant cells, insect cells and bacterial cells such as *E. coli*.

The present invention may also be directed to an isolated and purified disulfide bond formation protein from bacteria of the genus *Ehrlichia*, wherein said disulfide bond formation protein is encoded by the DNA described above. Preferably, the protein has a thio-disulfide oxidoreductase enzymatic activity. In specific embodiments, the protein may comprise an *Ehrlichia chaffeensis* disulfide bond formation protein such as that disclosed in SEQ ID No: 4 or an *Ehrlichia canis* disulfide bond formation protein such as that provided in SEQ ID No: 5.

In another embodiment of the invention described herein, antibodies against *Ehrlichia* disulfide bond formation proteins are provided. These antibodies may comprise either monoclonal antibodies or polyclonal antisera.

The instant invention also teaches a method of determining whether an animal or individual has been infected with a species of bacteria of the *Ehrlichia* genus. This method is accomplished by determining whether serum from said animal or individual reacts with a disulfide bond formation protein from said species of *Ehrlichia*. Recombinant disulfide bond formation proteins may be used in this assay, and reactions between the protein and antisera may be detected by Western blot analysis or other immunochemical methods. To ease the effort required by those of skill in the art in performing this assay, a serodiagnostic kit may be provided which includes: a) an immobilized *Ehrlichia* disulfide bond formation protein; b) appropriate dilution buffers for serum; c) an anti-serum second antibody linked to a reporter molecule; and d) appropriate reagents for detection of said reporter molecule. The *Ehrlichia* disulfide bond formation protein may be immobilized on a membrane or a microtiter plate. Possible reporter molecules include luciferase, horseradish peroxidase, β-galactosidase and fluorescent labels.

An alternative method of determining whether an animal or individual has been infected with a species of bacteria of the *Ehrlichia* genus is also provided, consisting of extracting DNA from the blood of said animal or individual, performing PCR amplification on said DNA with oligonucleotide primers specific for a dsb gene, and separating the resulting PCR products by size, wherein positive detection of an appropriately sized amplification product indicates *Ehrlichia* infection. Detection of the PCR product may be accomplished by gel electrophoresis. When the species of bacteria is *Ehrlichia chaffeensis*, PCR amplification may be performed using SEQ ID No.: 12, SEQ ID No. 15 and/or SEQ ID No. 17 as the forward primer(s) and SEQ ID No. 13 and/or SEQ ID No. 16 as the reverse primer(s). Forward primer SEQ ID No. 18 and reverse primer SEQ ID No. 19 are effective for the PCR amplification of *Ehrlichia canis* dsb. Alternative primers can be readily designed by those of skill in the art. A kit consisting of reagents for DNA extraction from blood, dsb-specific oligonucleotides, and reagents for PCR amplification may be provided to facilitate the application of this method in a clinical setting.

Yet another embodiment of the instant invention relates to vaccines against individual species of bacteria from the Ehrlichia genus. Such vaccines are prepared by inactivating the dsb gene in *Ehrlichia* bacteria to form attenuated strains. Methods of inactivating the disulfide bond formation gene include deletion of the gene itself, mutation of regulatory sequences necessary for expression of the dsb gene, expression of antisense RNA against dsb, and mutations which inactivate the Dsb protein encoded by the dsb gene. The vaccine may be directed against *Ehrlichia chaffeensis* and used to prevent or treat human monocytotropic ehrlichiosis (HME). Alternatively, the vaccine may be directed against *Ehrlichia canis* and used to prevent or treat canine monocytic ehrlichiosis (CME).

The following examples are given for the purpose of illustrating various embodiments of the invention and are not meant to limit the present invention in any fashion.

EXAMPLE 1

*Ehrlichia* and *E. coli* Strains

*Ehrlichia chaffeensis* Arkansas strain and *Ehrlichia canis* Jake strain were provided by Jacqueline Dawson (Center for Disease Control and Prevention, Atlanta, Ga.) and Dr. Edward Breitschwerdt (College of Veterinary Medicine, North Carolina State University, Raleigh, N.C.) respectively. *Ehrlichia* were propagated and purified as described previously (7). *E. coli* strains JCB502 and JCB572 (JCB502 dsbA::kan1), kindly provided by J. Bardwell (University of Michigan), were used in the complementation experiments as reference and mutant strains, respectively (1). *E. coli* were cultured on LB medium at 37° C.

EXAMPLE 2

Isolation of *E. canis* and *E. chaffeensis* Dsb

The *E. canis* dsb was identified by immunologic screening of a Lambda Zap II *E. canis* genomic library. Construction and screening of the *E. canis* genomic library has been described previously (7). Primers used to amplify the *E. chaffeensis* dsb gene, including forward primer p27nc42 (5'-GAG ATT TCT ACT ATT GAC TTC-3') (SEQ ID No. 12) targeting the upstream noncoding region, and reverse primer ECa27-700r (5'-CAG CTG CAC CAC CGA TAA ATG TA-3') (SEQ ID No. 13), were designed from sequences complementary to the *E. canis* dsb sequence. This primer pair amplified a region beginning upstream of the start codon through nucleotide 700 of the 738-bp open reading frame (ORF). The undetermined carboxy-terminus (38 bp) and the primer ECa27-700r annealing region (23 bp) of the *E. chaffeensis* dsb were obtained with primer ECf27-475 (5'-TTC TAC CAT GCT GCA CTA AAC C-3') (SEQ ID No. 14). Amplification was performed in the 3' direction using a genome walking kit (Clontech, Palo Alto, Calif.) as previously described (19).

EXAMPLE 3

Cloning, Expression and Sequencing of *Ehrlichia* rDsb Proteins

The entire *E. chaffeensis* dsb open reading frame was PCR amplified with primers Ech27f (5'-ATG CTA AGG ATT TTA TTT TTA TTA-3') (SEQ ID No. 15) and Ech27r (5'-TCC TTG CTC ATC TAT TTT ACT TC-3') (SEQ ID No. 16). The resulting amplification product was cloned directly into the pCR T7/CT TOPO TA expression vector (Invitrogen, Carlsbad, Calif.), that is designed to produce proteins with a native N-terminus and a carboxy-terminal polyhistidine region for purification. The resulting construct was designated pECf-dsb. *E. chaffeensis* and *E. canis* dsb genes without native N-terminus signal peptide encoding regions (ECh +75-bp; ECa +73-bp) were amplified by PCR using forward primers ECh27-75 (5'-ATG AGC AAA TCT GGT AAA ACT AT-3') (SEQ ID No. 17) and ECa27-73 (ATG TCT AAT AAA TCT GGT AAG C-3') (SEQ ID No. 18), respectively, and reverse primers ECh27r and ECa27r (5'-TTT CTG CAT ATC TAT TTT AC-3') (SEQ ID No. 19), respectively. The resulting products were cloned into pCR T7/CT TOPO TA, and the resulting N-terminal signal peptide-deficient expression vectors were designated pECf-Dsb-sp and pECa-Dsb-sp. All of the inserts were sequenced with an ABI Prism 377 DNA Sequencer (Perkin-Elmer Applied Biosystems, Foster City, Calif.). The *Ehrlichia* Dsb proteins were expressed in BL21 Star (DE3) pLysS *E. coli* and purified under denaturing conditions as described previously (7). The expressed recombinant proteins were used for antibody production and Western blotting experiments.

EXAMPLE 4

Complementation of *E. coli* dsbA Defective Mutants

The *E. coli* dsbA mutant JCM572 strain was used in complementation studies with JCM502 as the reference strain (1). The mutant JCM572 strain carries a kanamycin insertion in the dsbA gene, and is immotile due a defect in flagellar assembly related to disulfide bond formation in the flagellar P-ring protein (2). Expression constructs pECf-Dsb and pECf-Dsb-sp containing the complete and signal peptide-deficient *E. chaffeensis* dsb constructs, and a expression plasmid control (pCR T7/CT-LacZ), were electroporated (2.5 kV, 25 µF, 200 Ω) into *E. coli* strain JCM572 and selected on LB plates with 100 µg of ampicillin. Mutants were screened for motility on soft agar LB plates (0.22%) for 18 hr at 37° C. AP activity was determined from cells cultured in minimal medium and calculated using the formula: ([optical density at 420 nm with substrate—optical density at 420 nm without substrate]/min)×$10^3$ as described previously (5).

EXAMPLE 5

Detection and Immunoreactivity of *Ehrlichia* rDsb Proteins

Monospecific polyclonal antiserum to *E. chaffeensis* rDsb was produced by immunizing a rabbit with purified recombinant disulfide bond formation protein in Freund's complete adjuvant (FCA), followed by two booster immunizations in Freund's incomplete adjuvant (FIA). Monospecific polyclonal antiserum to *E. canis* rDsb was produced similarly by immunizing a mouse. Sera were tested by IFA to determine reactivity prior to immunoblotting and immunoelectron microscopy studies.

Expressed recombinant *E. chaffeensis* and *E. canis* Dsbs were subjected to sodium dodecylsulfate-polyacrylamide electrophoresis (SDS-PAGE) and transferred to pure nitrocellulose using a semidry electroblotting cell (BioRad, Hercules, Calif.). The membrane was blocked for 1 hr in 1% nonfat milk and incubated with rabbit anti-*E. chaffeensis* rDsb or mouse anti-*E. canis* recombinant disulfide bond formation protein. A secondary AP-labeled anti-mouse or rabbit IgG affinity-purified conjugate (1:5000) (Kirkegaard & Perry Laboratories, Gaithersburg, Md.) was used to detect bound anti-Dsb antibody. The immunoreactivity of the disulfide bond formation proteins with canine monocytic ehrlichiosis (CME) dog sera and human monocytotropic ehrlichiosis (HME) patient sera was also determined in a similar manner. A secondary AP-labeled goat anti-dog or anti-human IgG (H and L chains), affinity purified conjugate (Kirkegaard & Perry Laboratories) was used to detect bound antibody. Bound antibody was visualized with 5-bromo-4-chloro-indolyl-phosphatase/nitrotetrazolium blue substrate (Kirkegaard & Perry Laboratories).

EXAMPLE 6

Immunoelectron Microscopy

Fixation, LR white embedding and post embedding staining of ultrathin sections of DH82 cells infected with *E. chaffeensis* and *E. canis* were performed as described previously (14). Ultrathin sections treated in blocking buffer, (0.1% bovine serum albumin [BSA] and 0.01 M glycine in Tris buffer saline, [TBS]) were incubated with rabbit anti-*E. chaffeensis* recombinant disulfide bond formation protein polyclonal antibody diluted 1:100 in diluting buffer (1% BSA in TBS), then washed in blocking buffer, followed by incubation with goat anti-rabbit IgG (H and L chains) labeled with 15 nm colloidal gold particles (AuroProbe EM GAR G15, RPN422; Amersham Life Science, Arlington Heights, Ill.) diluted 1:20 in diluting buffer.

EXAMPLE 7

Protein Analysis

*Ehrlichia* Dsb amino acid sequences were analyzed by the method of Neilsen et. al., (13) for signal sequence recognition using SignalP (V 1.1) at the Center for Biological Sequence Analysis Internet site. Homologous domain architecture was determined using the domain architecture retrieval tool (DART) with reverse position specific BLAST of the conserved domain database (CDD) at the National Center of Biotechnology Information (NCBI) web page. *C. burnetii* Com1 and *E. coli* DsbA and DsbC sequences were obtained from the NCBI Internet site. Nucleotide and deduced amino acid sequences, protein hydrophilicity, antigenic index, and surface probability were determined with LASERGENE software V5.0 (DNASTAR, Inc., Madison, Wis.), based on the Kyte-Doolittle, Jameson Wolf and Emini algorithms.

EXAMPLE 8

Nucleotide Sequence Accession Numbers

The nucleotide sequence data for the E. chaffeensis and E. canis dsb genes were submitted to the NCBI nucleotide sequence database under accession numbers AF403710 and AF403711, respectively.

EXAMPLE 9

Identification of the E. canis and E. chaffeensis dsb Genes

Screening the E. canis genomic library with anti-E. canis immune sera identified an immunoreactive 2.4-kb clone. One complete and a second incomplete open reading frame (ORF) 42 bp downstream on the complementary strand are present in this 2.4-kb clone. The second open reading frame was disrupted by the HinP1I/HpaII cutting site used to construct the library, but encoded a protein of at least 309 amino acids (open reading frame-309). A search of available non-redundant nucleic acid and protein databases did not identify any significant homologous sequences to open reading frame-309.

The majority (98%) of the E chaffeensis dsb gene sequence was amplified by PCR using primers designed from the E. canis dsb gene sequence. Approximately 61 bp of additional sequence on the carboxy-terminus was obtained by genome walking, which produced a 1.1-kb fragment starting at nucleotide 475 of the E. chaffeensis dsb and continuing in the 3' direction, providing the complete sequence. The E. chaffeensis and E. canis dsb genes were both 738 bp, encoding proteins of 246 amino acids with predicted molecular masses of 27.7 and 27.5 kDa, respectively. The nucleic acid homology between the Ehrlichia dsb genes was 84%, but there was no homology with any other database sequences (FIG. 1).

EXAMPLE 10

Ehrlichia Dsb Protein Analysis

A conserved amino acid domain from the thioredoxin superfamily was identified in the Ehrlichia disulfide bond formation proteins, which were most similar to E. coli DsbA according to DART. A conserved cysteine active site identical to the active site of E. coli DsbC is present in the Ehrlichia disulfide bond formation protein (FIGS. 2 and 3). The Ehrlichia disulfide bond formation proteins were 87% homologous to each other and shared some homology with Coxiella burnetii Com1 (31%) (FIG. 2). Amino acid sequence analysis using the SignalP prediction server predicted that the Ehrlichia disulfide bond formation proteins have identical 15-amino acid hydrophobic N-terminal signal peptide sequences consisting of the sequence MLRILFLLSLVILVA (SEQ ID No. 19) (FIG. 2). The predicted molecular masses of the mature E. chaffeensis and E. canis Dsb proteins are 25.5 and 25.8 kDa, respectively.

Comparison of the Ehrlichia Dsb proteins, C. burnetii Com1, and periplasmic E. coli DsbA identified conservation in hydrophilicity, antigenic index and surface probability among these proteins (FIG. 4). Hydrophilicity plots revealed strong similarity among Ehrlichia Dsb proteins, Com1 and DsbA, including a hydrophobic leader sequence. In contrast, cytoplasmic membrane protein DsbB of E. coli has very few hydrophilic regions, but has hydrophobic regions indicative of membrane spanning proteins (FIG. 4). The cysteine active site of the Ehrlichia disulfide bond formation proteins is located in a hydrophobic region and was not surface exposed according to the Kyte-Doolittle plots. Antigenic index correlates with the predicted surface exposed and hydrophilic regions of the proteins.

EXAMPLE 11

Expression and Immunoreactivity of Ehrlichia rDsb Proteins

Figure 7A:
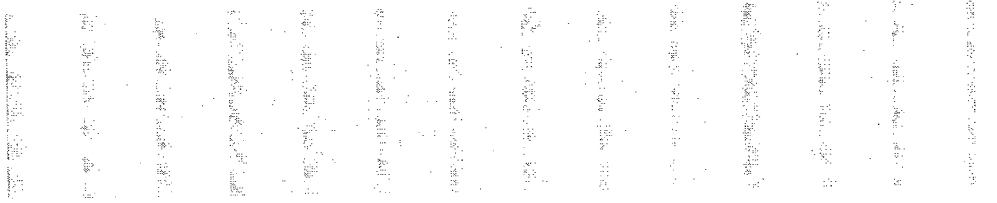
Figure 7B:
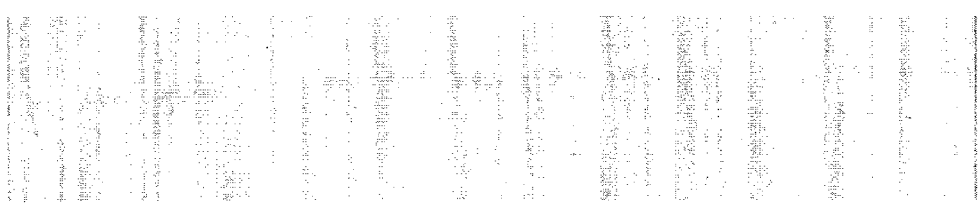
Figure 7C:
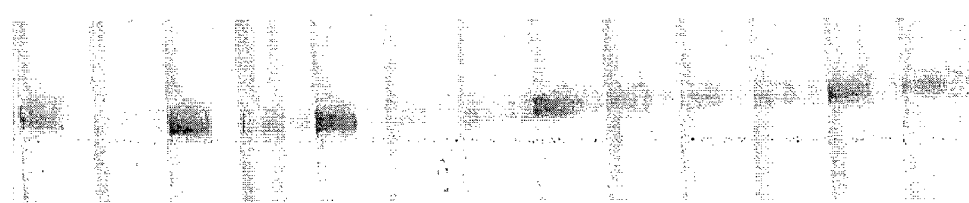
Figure 8A:
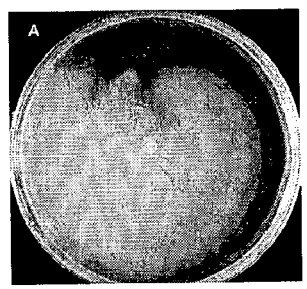
Figure 8B:
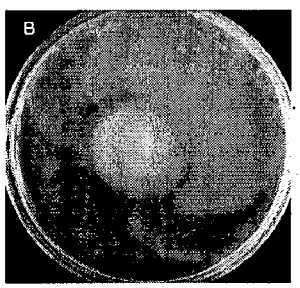
Figure 8C:
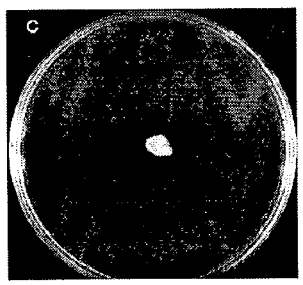
Figure 8D:
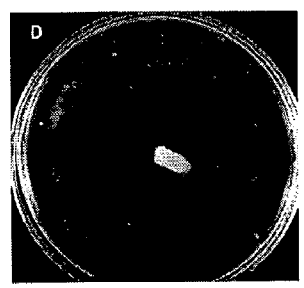

Ehrlichia rDsb proteins were expressed without the N-terminus region (25 amino acids) including the predicted 15-amino acid signal peptide (FIG. 5A). The purified rDsb proteins migrated at approximately 23 kDa (FIG. 5A), which accounted for the C-terminal fusion tag (5 kDa), and coincided with the predicted molecular mass. The Ehrlichia rDsbs were detected by immunoblot with rabbit anti-E. chaffeensis rDsb and mouse anti-E. canis rDsb (FIGS. 5B and C). The Ehrlichia disulfide bond formation proteins were immunoreactive with homologous recombinant disulfide bond formation protein antiserum, and exhibited crossreactivity with the heterologous antiserum (FIGS. 5B and C). Antibody against the E. chaffeensis rDsb proteins reacted with native proteins in the whole cell lysates of E. chaffeensis (26 kDa) and E. canis (25 kDa) (FIG. 6). Sera from dogs with canine monocytic ehrlichiosis reacted strongly with the E. canis rDsb and exhibited weaker cross-reactivity with the E. chaffeensis rDsb (FIG. 7). Immune sera from human monocytotropic ehrlichiosis patients that contained antibodies to E. chaffeensis detected by IFA did not react with the E. chaffeensis rDsb (FIG. 7).

EXAMPLE 12

Complementation of E. coli dsbA Defective Mutants

E. chaffeensis dsb gene constructs of the complete ORF, pECf-Dsb, and constructs excluding the N-terminal signal peptide region, pECf-Dsb-sp, were electroporated into E. coli strain JCM572. A plasmid control expressing the lacZ gene was used as a negative control in the E. coli dsbA mutants. Complementation with the JCB572 [pECf-Dsb] gene construct resulted in the restoration of motility in the normally non-motile E. coli dsbA mutant similar to that observed in the reference strain, JCM502. Motility was not restored using the JCB572 [pECf-Dsb sp] gene construct, which lacked 25 amino acids on the N-terminus of the protein including the predicted 15-amino acid signal peptide, or with the lacZ plasmid control (FIG. 8).

Figure 9:
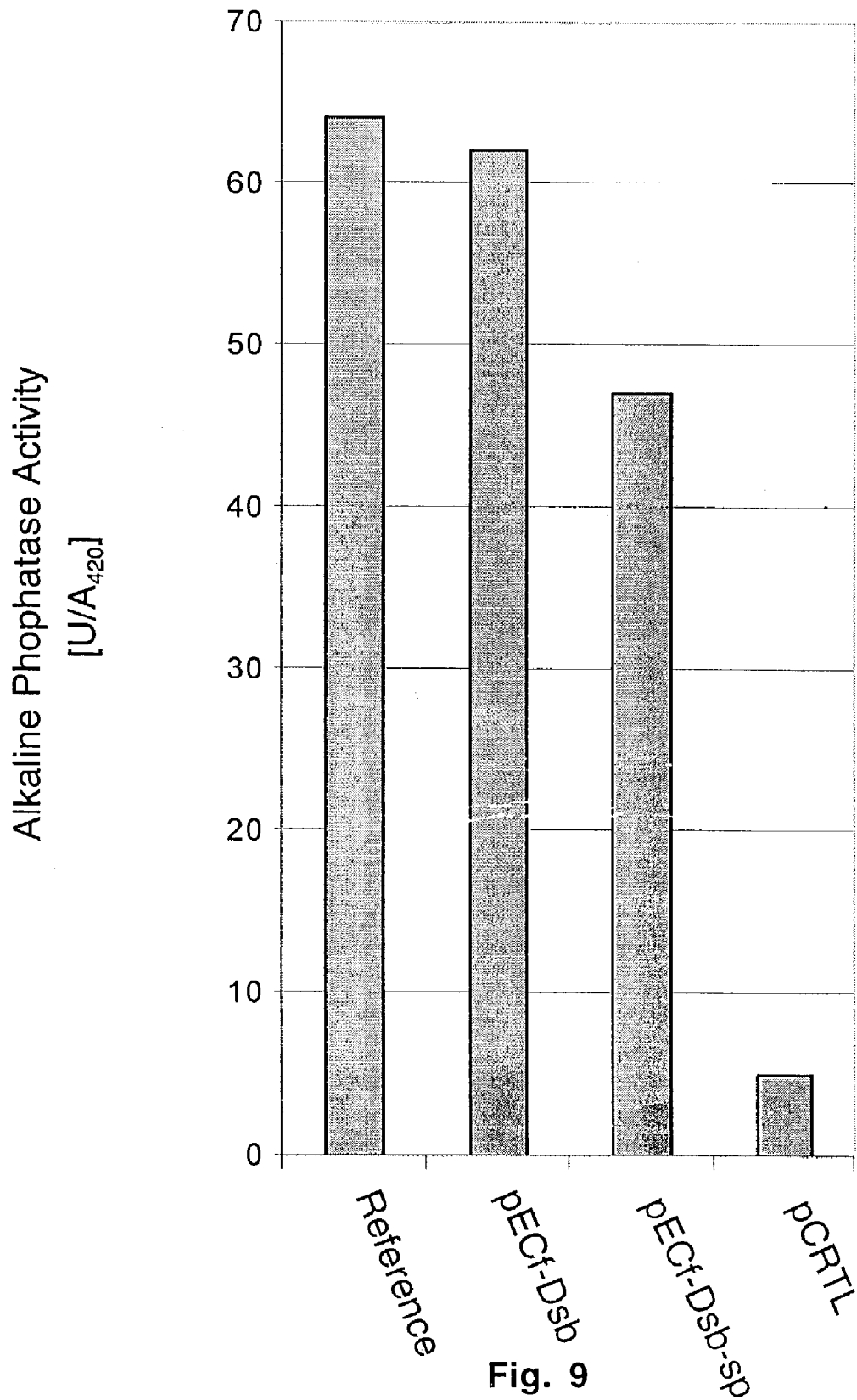

Alkaline phosphatase is a disulfide bonded periplasmic enzyme, and disulfide bonds must be formed for its proper folding and activity. Decreased alkaline phosphatase activity in dsbA mutants has been reported (6). To confirm the disulfide bond formation activity demonstrated in the motility experiments, alkaline phosphatase activity in the wild type was compared with that in the E. chaffeensis dsb-complemented E. coli dsbA mutants. Reference strain JCB502 and mutant strain JCB572 transfected with pECf-Dsb (JCB572 [pECf-Dsb]) exhibited similar alkaline phosphatase activity. Mutant strain JCB572 [pECf-Dsb-sp] had approximately 30% lower alkaline phosphatase activity, and the plasmid control, JCB572 [pLacZ] had very low alkaline phosphatase activity (FIG. 9).

EXAMPLE 13

Figure 10A:
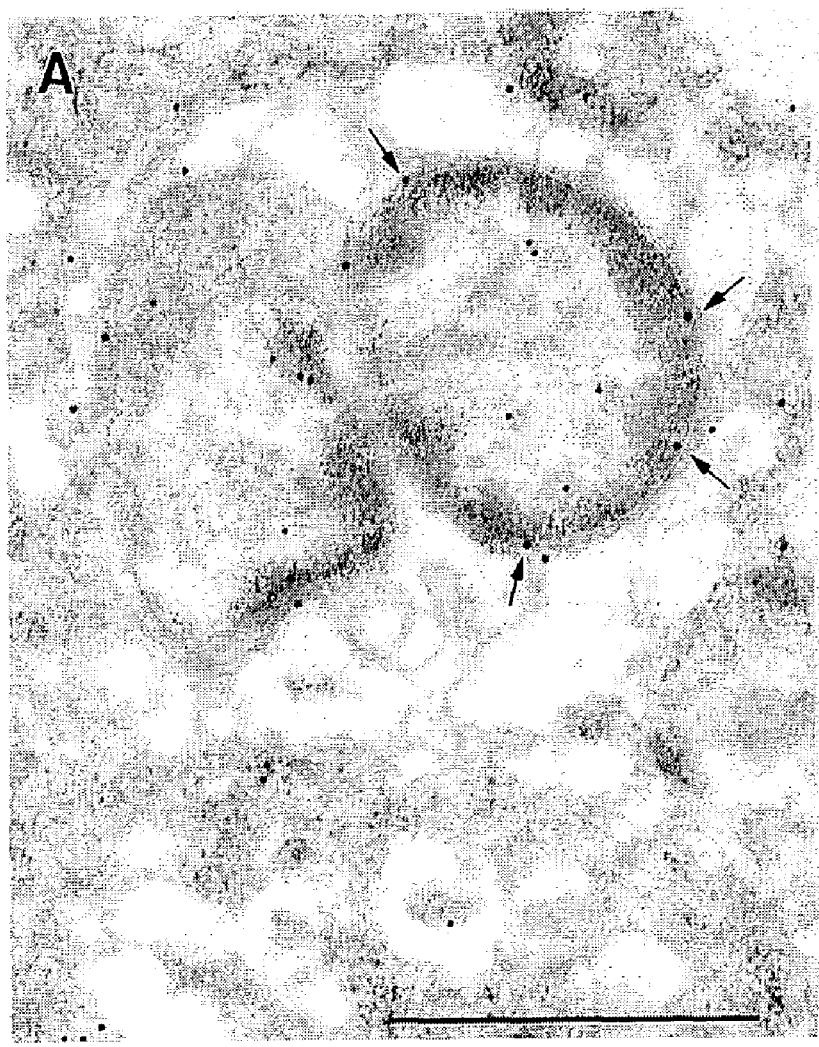
Figure 10B:
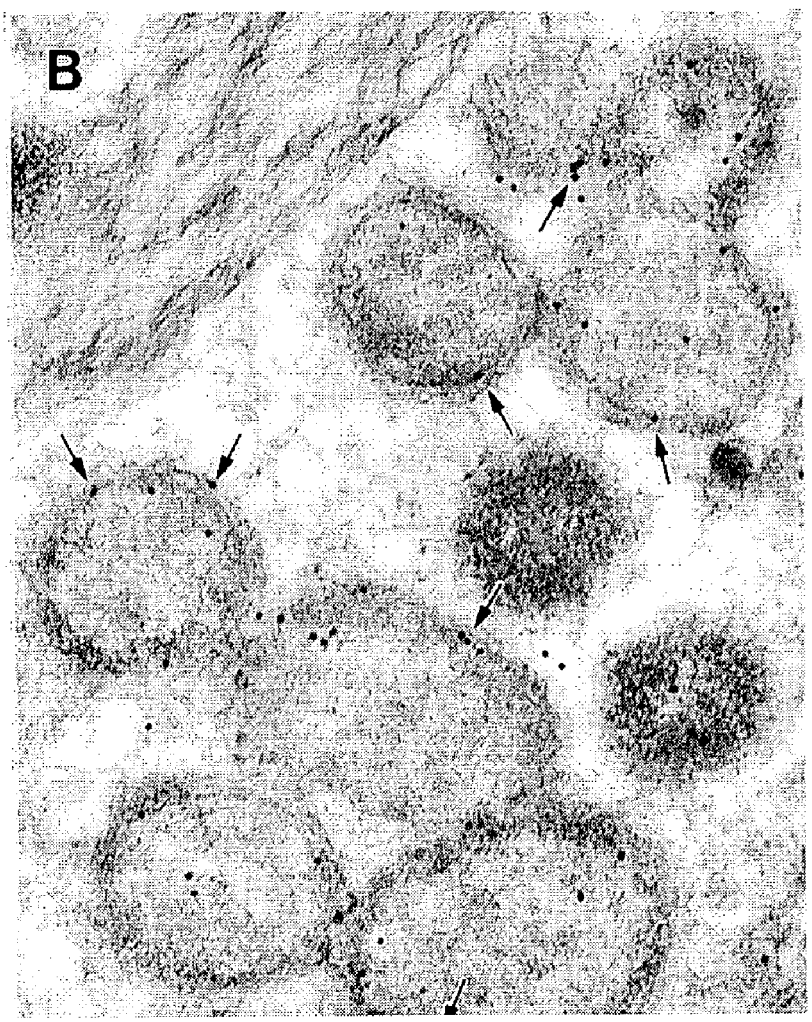

Cellular Location of the Dsb Protein DH82 cells infected with *E. chaffeensis* and *E. canis* were incubated with rabbit anti-*E. chaffeensis* rDsb. Disulfide bond formation protein was identified primarily in the cytoplasmic membrane/periplasm region, with most label appearing to be in the periplasmic space of both organisms. Cytoplasmic localization was observed, which is consistent with production and transport of disulfide bond formation protein from the cytoplasm to the periplasm, and occasional surface labeling was observed (FIG. 10). No difference was observed in the amount of *Ehrlichia* Dsb in dense-cored and reticulate cells.

Discussion

Little is known about the mechanism of disulfide bond formation and the role of inter- and intramolecular disulfide bonds in the overall cell envelope structure in *Ehrlichia*. This is the first report of a thio-disulfide oxidoreductase in *Ehrlichia* and provides evidence that disulfide bond formation occurs, perhaps playing an important role in the *Ehrlichia* life cycle and pathogenesis. Previous studies with the related agent, *Anaplasma marginale*, demonstrated the importance of intra- and intermolecular disulfide bonds in the supramolecular structure of the cell envelope (18). Disulfide bonds in *Chlamydiae* are involved in the development of ultrastructural forms of this organism (3), which are similar in appearance to the *Ehrlichia* reticulate and dense-cored forms (14).

The active site and domain architecture found in the *Ehrlichia* disulfide bond formation proteins suggest that they are more similar to the periplasmic disulfide bond formation proteins of *E. coli* than to cytoplasmic membrane disulfide bond formation proteins or cytoplasmic thioredoxin. The *Ehrlichia* dsb genes are not homologous to other known thio-disulfide oxidoreductase genes, but the encoded proteins do contain a conserved cysteine motif, Cys-Gly-Tyr-Cys (SEQ ID No. 7), which comprises the active site of other known disulfide oxidoreductases. The predicted amino acid sequence of the *Ehrlichia* disulfide bond formation protein active sites was identical to that of *E. coli* DsbC. The domain homology identified by DART also confirmed that the region containing the active site has a conserved architectural domain found in *E. coli* DsbA, which is common among other members of the thioredoxin superfamily.

Homology was observed between *Ehrlichia* Dsbs and *C. burnetii* Com1 (31%), which has a cysteine active site identical to thioredoxin, but contains a predicted signal sequence that is not found in thioredoxin (4). Hydrophilicity and surface probability plots suggest that the *Ehrlichia* Dsbs, *C. burnetii* Com1 and periplasmic *E. coli* DsbA are homologous. One strong and several weak hydrophobic regions were observed in the *Ehrlichia* Dsb proteins, *C. burnetti* Com1 and *E. coli* DsbA, which thus differed from *E. coli* DsbB, which is a cytoplasmic membrane spanning protein that has very few hydrophilic regions and increased hydrophobicity. Although the location of *C. burnetii* Com1 has not been definitively determined, it is Sarkosyl-soluble, which is a property of cytoplasmic membrane and periplasmic proteins (4).

This observation is consistent with the location reported for the *E. coli* disulfide bond formation proteins, since *Ehrlichia* disulfide bond formation proteins appear to be most abundant in the periplasm. This finding supports complementation experiments in which *E. chaffeensis* dsb complemented the *E. coli* dsbA mutant, strongly suggesting that the *Ehrlichia* disulfide bond formation proteins are orthologs of periplasmic DsbA. It is possible, however, that the *Ehrlichia* disulfide bond formation proteins are DsbC orthologs, as dsbC has also been shown to complement a defective dsbA gene. The compilation of the findings reported herein supports that the *Ehrlichia* disulfide bond formation proteins are orthologs of the periplasmic *E. coli* DsbA or DsbC. Identification of additional disulfide bond formation proteins in *Ehrlichia* would help confirm the specific identity of this *Ehrlichia* disulfide bond formation protein.

The function of the *Ehrlichia* disulfide bond formation proteins appears to require the N-terminal sequence. The *E. chaffeensis* disulfide bond formation protein, which is deficient in the N-terminal signal peptide region (24 amino acids), did not complement the *E. coli* dsbA mutants in the motility assay. Also, AP activity was reduced in the clones without the N-terminus. These experiments appear to confirm that the signal sequence identified by SignalP serves to transport the disulfide bond formation protein from the cytoplasm across the cytoplasmic membrane. All of the *E. coli* disulfide bond formation proteins with the exception of thioredoxin are membrane or periplasmic proteins. Therefore, it was expected that mutants complemented with the N-terminus deficient protein would lack activity. There have been other thio-disulfide oxidoreductases cloned from various bacteria that contain predicted signal sequences and complement *E. coli* dsbA mutants (5,12). Furthermore, proteins transported to the cytoplasmic membrane, periplasm, or outer membrane typically have signal peptide sequences (13). This is the first report demonstrating that *Ehrlichia* signal peptides are recognized by *E. coli* and appear to be translocated to proper cellular locations in *E. coli*.

The location of the *Ehrlichia* disulfide bond formation proteins suggests that they may potentially be immunoreactive. Although the *E. canis* disulfide bond formation was identified by screening an expression library with antibody, it was possible that the reactivity of this clone could be attributed to the second ORF in the clone containing the dsb gene. The expressed *E. canis* disulfide bond formation protein did, however, react with convalescent sera from dogs naturally infected with *E. canis*, indicating that the *E. canis* disulfide bond formation is targeted by the immune response. However, antibodies from HME patients did not react with the *E. chaffeensis* disulfide bond formation protein, suggesting that this protein is not a major target during the acute phase immune response.

The response to disulfide bond formation protein by *E. canis*-infected dogs suggests that an immune response to the protein may develop if the infection is longer in duration or persistent. It is also unlikely that the disulfide bond formation protein is responsible for cross-reactive antibodies to other *Ehrlichia* in HME-infected patients, although antibodies to disulfide bond formation protein detected in *E. canis*-infected dog sera would contribute to cross-reactivity with *E. chaffeensis*. The high nucleic and amino acid homology of the disulfide bond formation proteins suggest that cross-reactive epitopes would be present. Antisera raised specifically against the *E. chaffeensis* rDsb reacted equally with the *E. canis* rDsb by Western blot, although differences in the reactivity of dog sera to the heterologous proteins were readily apparent. This observation may be related to differences in antibody titer between the sera from dogs compared to that of the hyperimmune rabbit sera and indicates that immunologically these disulfide bond formation proteins have some homologous and heterologous epitopes. The apparent role of Dsb in cell envelope structure suggests that it could be an important target of the immune response. Further studies should be performed to provide information on the immunoprotective role of disulfide bond formation proteins.

E. coli disulfide bond formation proteins provide some information regarding the possible role of *Ehrlichia* Dsb proteins. Studies to determine the role of disulfide bonds in cell envelope structure and cell ultrastructure are providing additional insights into the role of disulfide bond formation proteins in the *Ehrlichia* life cycle and pathogenesis.

The following references were cited herein:
1. Bardwell, J. C., K. McGovern, and J. Beckwith. 1991. Identification of a protein required for disulfide bond formation in vivo. *Cell* 67:581-589.
2. Dailey, F. E. and H. C. Berg. 1993. Mutants in disulfide bond formation that disrupt flagellar assembly in *Escherichia coli*. *Proc. Natl. Acad. Sci.* 90:1043-1047.
3. Hatch, T. P., I. Allan, and J. H. Pearce. 1984. Structural and polypeptide differences between envelopes of infective and reproductive life cycle forms of *Chlamydia* spp. *J. Bacteriol.* 157:13-20.
4. Hendrix, L. R., L. P. Mallavia, and J. E. Samuel. 1993. Cloning and sequencing of *Coxiella burnetii* outer membrane protein gene com1. *Infect. Immun.* 61:470-477.
5. Ishihara, T., H. Tomita, Y. Hasegawa, N. Tsukagoshi, H. Yamagata, and S. Udaka. 1995. Cloning and characterization of the gene for a protein thiol-disulfide oxidoreductase in *Bacillus brevis*. *J. Bacteriol.* 177:745-749.
6. Kamitani, S., Y. Akiyama, and K. Ito. 1992. Identification and characterization of an *Escherichia coli* gene required for the formation of correctly folded alkaline phosphatase, a periplasmic enzyme. *EMBO J.* 11:57-62.
7. McBride, J. W., R. E. Corstvet, E. B. Breitschwerdt, and D. H. Walker. 2001. Immunodiagnosis of *Ehrlichia canis* infection with recombinant proteins. *J. Clin. Microbiol.* 39:315-322.
8. Missiakas, D., C. Georgopoulos, and S. Raina. 1993. Identification and characterization of the *Escherichia coli* gene dsbB, whose product is involved in the formation of disulfide bonds in vivo. *Proc. Natl. Acad. Sci.* 90:7084-7088.
9. Missiakas, D., C. Georgopoulos, and S. Raina. 1994. The *Escherichia coli* dsbC (xprA) gene encodes a periplasmic protein involved in disulfide bond formation. *EMBO J.* 13:2013-2020.
10. Missiakas, D. and S. Raina. 1997. Protein folding in the bacterial periplasm. *J. Bacteriol.* 179:2465-2471.
11. Missiakas, D., F. Schwager, and S. Raina. 1995. Identification and characterization of a new disulfide isomerase-like protein (DsbD) in *Escherichia coli*. *EMBO J.* 14:3415-3424.
12. Ng, T. C., J. F. Kwik, and R. J. Maier. 1997. Cloning and expression of the gene for a protein disulfide oxidoreductase from *Azotobacter vinelandii*: complementation of an *Escherichia coli* dsbA mutant strain. *Gene* 188:109-113.
13. Nielsen, H., J. Engelbrecht, S. Brunak, and G. von Heijne. 1997. Identification of prokaryotic and eukaryotic signal peptides and prediction of their cleavage sites. *Protein Eng.* 10: 1-6.
14. Popov, V. L., S. M. Chen, H. M. Feng, and D. H. Walker. 1995. Ultrastructural variation of cultured *Ehrlichia chaffeensis*. *J. Med. Microbiol.* 43:411-421.
15. Popov, V. L., V. C. Han, S. M. Chen, J. S. Dumler, H. M. Feng, T. G. Andreadis, R. B. Tesh, and D. H. Walker. 1998. Ultrastructural differentiation of the genogroups in the Genus *Ehrlichia*. *J. Med. Microbiol.* 47:235-251.
16. Raina, S. and D. Missiakas. 1997. Making and breaking disulfide bonds. *Annu. Rev. Microbiol.* 51:179-202.
17. Russel, M. and P. Model. 1986. The role of thioredoxin in filamentous phage assembly. Construction, isolation, and characterization of mutant thioredoxins. *J. Biol. Chem.* 261:14997-15005.
18. Vidotto, M. C., T. C. McGuire, T. F. McElwain, G. H. Palmer, and D. P. Knowles, Jr. 1994. Intermolecular relationships of major surface proteins of *Anaplasma marginale*. *Infect. Immun.* 62:2940-2946.
19. Yu, X. J., J. W. McBride, X. F. Zhang, and D. H. Walker. 2000. Characterization of the complete transcriptionally active *Ehrlichia chaffeensis* 28 kDa outer membrane protein multigene family. *Gene* 248:59-68.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of determining whether an animal or individual has been infected with a species of bacteria of the *Ehrlichia* genus, comprising the step of performing PCR amplification on DNA from the blood of the animal with oligonucleotide primers specific for a disulfide bond formation (dsb) polynucleotide, wherein positive detection of an amplification product indicates *Ehrlichia* infection.

2. The method of claim 1, wherein said species of bacteria is *Ehrlichia chaffeensis*.

3. The method of claim 2, wherein the PCR amplification is performed with a primer selected from the group consisting of SEQ ID No:12, SEQ ID No:15, SEQ ID No:17, SEQ ID No:13 and SEQ ID No:16.

4. The method of claim 1, wherein said species of bacteria is *Ehrlichia canis*.

5. The method of claim 4, wherein the PCR amplification is performed with primer SEQ ID No:18 or primer SEQ ID No:19.

6. The method of claim 1, further defined as comprising the step of extracting DNA from the blood of said animal or individual.

7. The method of claim 1, further defined as comprising the step of separating the resulting PCR products by size.

8. The method of claim 7, wherein said PCR products are detected by gel electrophoresis.

* * * * *

SEQUENCE LISTING

```
<160> NUMBER OF SEQ ID NOS: 20

<210> SEQ ID NO 1
<211> LENGTH: 4
<212> TYPE: PRT
<213> ORGANISM: unknown
<220> FEATURE:
<221> NAME/KEY: DOMAIN
<222> LOCATION: 2, 3
<223> OTHER INFORMATION: Conserved cysteine motif in a thioredoxin
      active site, characterized in various bacteria; Xaa at positions
      2 and 3 are any amino acids

<400> SEQUENCE: 1

Cys Xaa Xaa Cys
```

<210> SEQ ID NO 2
<211> LENGTH: 738
<212> TYPE: DNA
<213> ORGANISM: Ehrlichia chaffeensis
<220> FEATURE:
<221> NAME/KEY: gene
<223> OTHER INFORMATION: Ehrlichia chaffeensis DNA sequence for
      disulfide bond formation gene

<400> SEQUENCE: 2

| | | |
|---|---|---|
| atgctaagga tttattttt attaagttta gttatactag tagcaagctt | 50 |
| tccgttaata aacaattggt tatctagcaa atctggtaaa actataatag | 100 |
| ataaagatac aattatctca atcgtagaag aatatattgc taattaccct | 150 |
| caaaaagtca ttgacctcct aactagaggg caagcacaag cagaaaatga | 200 |
| agaaatcgtt aaaaacataa aaagtataa atctgaactt gaggatagct | 250 |
| catatccttc tgcaggaaat aaagacagta aaatcgtatt tgtagaattc | 300 |
| tttgattact cttgtggtta ttgcaaaatg atgtctgaag atatgaaaca | 350 |
| aataatacaa gatggtaaag tacgtgtcat atttagagat tttccaatac | 400 |
| ttggagaagc atcactgaaa gctgttcaag cagcactagc agtacatcta | 450 |
| ataaacccaa gtaaatacat cgagttctac catgctgcac taaaccataa | 500 |
| gcagcaattt aacgatgaat ctatactaag tctagtcaaa tcaataggta | 550 |
| ttgctgaaga agattttaaa gtttcattag ccaagaattc cgacactata | 600 |
| gaaaaaatga tacaatctac taagaattta gctcaaaaca ttaacataag | 650 |
| gggcacccct cgcattataa taggagatac atttattggt ggagcagctg | 700 |
| atatatctac tttaagaagt aaaatagatg agcaagga | 738 |

<210> SEQ ID NO 3
<211> LENGTH: 738
<212> TYPE: DNA
<213> ORGANISM: Ehrlichia canis
<220> FEATURE:
<221> NAME/KEY: gene
<222> LOCATION: 13, 27, 33, 42, 48, 54, 55, 63, 66, 77, 78,
      90, 91, 97, 117, 118, 123, 124, 126, 138, 139,
      141, 159, 162, 165, 168, 171, 174, 176, 185,
      186, 188, 189, 195, 211, 225, 228, 238, 240,
      243, 244, 248, 249, 261, 264, 276, 285, 297,
      312, 315, 318, 355, 363, 372, 374, 378, 384,
      405, 408, 410, 411, 417, 422, 425, 426, 441,
      448, 450, 453, 456, 461, 465, 471, 474, 480,
      481, 486, 493, 495, 496, 498, 504, 507, 513,
      519, 522, 526, 532, 534, 535, 537, 552, 553,
      564, 567, 573, 582, 585, 589, 591, 594, 595,
      603, 621, 623, 628, 633, 636, 645, 657, 663,
      666, 670, 675, 687, 693, 708, 730, 731, 735,
      736, 737
<223> OTHER INFORMATION: Ehrlichia canis DNA sequence for disulfide
      bond formation gene; n = a, t, c, or g at
<220> FEATURE:
<222> LOCATION:

<400> SEQUENCE: 3

| | | |
|---|---|---|
| atgctaagga ttntattttt attaagntta gtnatactag tngcaagntt | 50 |
| tccnntaata aanaantggt tatctannaa atctggtaan nctatantag | 100 |
| ataaagatac aattatnnca atnntngaag aatatatnnc naattaccct | 150 |
| caaaaagtna tnganctnct nacnanaggg caagnncnng cagananatga | 200 |
| agaaatgagt naaaacataa aaaantanaa atctgaantn gannatannt | 250 |

-continued

```
catatccttc ngcnggaaat aaaganagta aaatngtatt tgtaganttc        300
tttgattact cntgnggnta ttgcaaaatg atgtctgaag atatgaaaca        350
aatantacaa ganggtaaag tncntgtnat attnagagat tttccaatac        400
ttggngancn ntcactnaaa gntgnncaag cagcactagc ngtacatntn        450
atnaanccaa ntaantacat nganttctan natgcngcac tanannanaa        500
gcancanttt aangatgant cnatantaag tntnnntnaaa tcaataggta       550 tnnctgaaga aganttnaaa gtntcattag cnaanaatnc ngannctata       600
ganaaaatga tacaatctac nanagaanta gcncanaaca ttaanataag       650
gggcacncct gcnatnatan taggngatac atttatnggt ggngcagctg       700
atatatcnac tttaagaagt aaaatagatn ngcannna                    738
```

```
<210> SEQ ID NO 4
<211> LENGTH: 246
<212> TYPE: PRT
<213> ORGANISM: Ehrlichia chaffeensis
<220> FEATURE:
<223> OTHER INFORMATION: Ehrlichia chaffeensis amino acid sequence
      for disulfide bond formation protein

<400> SEQUENCE: 4

Met Leu Arg Ile Leu Phe Leu Leu Ser Leu Val Ile Leu Val Ala
              5                   10                  15

Ser Phe Pro Leu Ile Asn Asn Trp Leu Ser Ser Lys Ser Gly Lys
              20                  25                  30

Thr Ile Ile Asp Lys Asp Thr Ile Ile Ser Ile Val Glu Glu Tyr
              35                  40                  45

Ile Ala Asn Tyr Pro Gln Lys Val Ile Asp Leu Leu Thr Arg Gly
              50                  55                  60

Gln Ala Gln Ala Glu Asn Glu Glu Met Ser Lys Asn Ile Lys Lys
              65                  70                  75

Tyr Lys Ser Glu Leu Glu Asp Ser Ser Tyr Pro Ser Ala Gly Asn
              80                  85                  90

Lys Asp Ser Lys Ile Val Phe Val Glu Phe Phe Asp Tyr Ser Cys
              95                  100                 105

Gly Tyr Cys Lys Met Met Ser Glu Asp Met Lys Gln Ile Ile Gln
              110                 115                 120

Asp Gly Lys Val Arg Val Ile Phe Arg Asp Phe Pro Ile Leu Gly
              125                 130                 135

Glu Ala Ser Leu Lys Ala Val Gln Ala Ala Leu Ala Val His Leu
              140                 145                 150

Ile Asn Pro Ser Lys Tyr Ile Glu Phe Tyr His Ala Ala Leu Asn
              155                 160                 165

His Lys Gln Gln Phe Asn Asp Glu Ser Ile Leu Ser Leu Val Lys
              170                 175                 180

Ser Ile Gly Ile Ala Glu Glu Asp Phe Lys Val Ser Leu Ala Lys
              185                 190                 195

Asn Ser Asp Thr Ile Glu Lys Met Ile Gln Ser Thr Lys Glu Leu
              200                 205                 210

Ala Gln Asn Ile Asn Ile Arg Gly Thr Pro Ala Ile Ile Ile Gly
              215                 220                 225

Asp Thr Phe Ile Gly Gly Ala Ala Asp Ile Ser Thr Leu Arg Ser
              230                 235                 240
```

Lys Ile Asp Glu Gln Gly
            245

<210> SEQ ID NO 5
<211> LENGTH: 246
<212> TYPE: PRT
<213> ORGANISM: Ehrlichia canis
<220> FEATURE:
<221> NAME/KEY: UNSURE
<222> LOCATION: 26, 31, 33, 40, 42, 47, 59, 62, 63, 71, 82,
        83, 119, 125, 137, 141, 142, 150, 154, 158,
        161, 165, 166, 178, 179, 185, 197, 199, 201,
        208, 224, 244, 246
<223> OTHER INFORMATION: Ehrlichia canis amino acid sequence
      for disulfide bond formation protein;
      Xaa is any amino acid at all positions
<220> FEATURE:
<222> LOCATION:

<400> SEQUENCE: 5

Met Leu Arg Ile Leu Phe Leu Leu Ser Leu Val Ile Leu Val Ala
              5                   10                  15

Ser Phe Pro Leu Ile Asn Asn Trp Leu Ser Xaa Lys Ser Gly Lys
             20                  25                  30

Xaa Ile Xaa Asp Lys Asp Thr Ile Ile Xaa Ile Xaa Glu Glu Tyr
             35                  40                  45

Ile Xaa Asn Tyr Pro Gln Lys Val Ile Asp Leu Leu Thr Xaa Gly
             50                  55                  60

Gln Xaa Xaa Ala Glu Asn Glu Glu Met Ser Xaa Asn Ile Lys Lys
             65                  70                  75

Tyr Lys Ser Glu Leu Glu Xaa Xaa Ser Tyr Pro Ser Ala Gly Asn
             80                  85                  90

Lys Asp Ser Lys Ile Val Phe Val Glu Phe Phe Asp Tyr Ser Cys
             95                 100                 105

Gly Tyr Cys Lys Met Met Ser Glu Asp Met Lys Gln Ile Xaa Gln
            110                 115                 120

Asp Gly Lys Val Xaa Val Ile Phe Arg Asp Phe Pro Ile Leu Gly
            125                 130                 135

Glu Xaa Ser Leu Lys Xaa Xaa Gln Ala Ala Leu Ala Val His Xaa
            140                 145                 150

Ile Asn Pro Xaa Lys Tyr Ile Xaa Phe Tyr Xaa Ala Ala Leu Xaa
            155                 160                 165

Xaa Lys Gln Gln Phe Asn Asp Glu Ser Ile Leu Ser Xaa Xaa Lys
            170                 175                 180

Ser Ile Gly Ile Xaa Glu Glu Asp Phe Lys Val Ser Leu Ala Lys
            185                 190                 195

Asn Xaa Asp Xaa Ile Xaa Lys Met Ile Gln Ser Thr Xaa Glu Leu
            200                 205                 210

Ala Gln Asn Ile Asn Ile Arg Gly Thr Pro Ala Ile Ile Xaa Gly
            215                 220                 225

Asp Thr Phe Ile Gly Gly Ala Ala Asp Ile Ser Thr Leu Arg Ser
            230                 235                 240

Lys Ile Asp Xaa Gln Xaa
            245

<210> SEQ ID NO 6
<211> LENGTH: 252
<212> TYPE: PRT
<213> ORGANISM: Coxiella burnetii

```
<220> FEATURE:
<221> NAME/KEY: UNSURE
<222> LOCATION: 1, 2, 3, 4, 6, 7, 11, 12, 13, 15, 17, 18,
      19, 20, 21, 22, 23, 25, 26, 27, 28, 29, 30,
      31, 32, 33, 34, 35, 37, 41, 42, 44, 45, 47,
      49, 50, 51, 52, 53, 54, 55, 56, 57, 59, 60,
      61, 62, 63, 64, 65, 66, 67, 69, 70, 71, 72,
      73, 76, 77, 78, 79, 80, 82, 83, 85, 86, 87,
      89, 93, 94, 95, 96, 97, 98, 99, 106, 109, 112,
      114, 115, 116, 117, 118, 119, 121, 122, 123,
      124, 126, 127, 130, 132, 133, 134, 137, 139,
      140, 142, 143, 145, 146, 147, 148, 151, 152,
      153, 154, 155, 158, 159, 161, 162, 164, 166,
      167, 168, 169, 171, 172, 173, 174, 175, 176,
      178, 179, 180, 181, 182, 183, 185, 186, 187,
      188, 189, 190, 192, 193, 194, 195, 196, 197,
      198, 200, 202, 203, 204, 205, 206, 207, 208,
      212, 213, 214, 215, 216, 220, 221, 222, 225,
      226, 227, 228, 229, 230, 231, 232, 235, 238,
      239, 240, 241, 242, 244, 245, 246, 249, 250,
      251, 252
<223> OTHER INFORMATION: Coxiella burnetii amino acid sequence
      for Com1 protein; Xaa is any amino acid
<220> FEATURE:
<222> LOCATION:

<400> SEQUENCE: 6

Xaa Xaa Xaa Xaa Leu Xaa Xaa Leu Phe Leu Xaa Xaa Xaa Leu Xaa
                 5                  10                  15

Ala Xaa Xaa Xaa Xaa Xaa Xaa Xaa Ser Xaa Xaa Xaa Xaa Xaa Xaa
                 20                  25                  30

Xaa Xaa Xaa Xaa Xaa Ile Xaa Ser Ile Val Xaa Xaa Tyr Xaa Xaa
                 35                  40                  45

Asn Xaa Pro Xaa Xaa Xaa Xaa Xaa Xaa Xaa Xaa Xaa Leu Xaa Xaa
                 50                  55                  60

Xaa Xaa Xaa Xaa Xaa Xaa Glu Xaa Xaa Xaa Xaa Xaa Ile Lys
                 65                  70                  75

Xaa Xaa Xaa Xaa Xaa Leu Xaa Xaa Asp Xaa Xaa Xaa Pro Xaa Ala
                 80                  85                  90

Gly Asn Xaa Xaa Xaa Xaa Xaa Xaa Xaa Val Glu Phe Phe Asp Tyr
                 95                 100                 105

Xaa Cys Gly Xaa Cys Lys Xaa Met Xaa Xaa Xaa Xaa Xaa Xaa Ile
                110                 115                 120

Xaa Xaa Xaa Xaa Lys Xaa Xaa Arg Val Xaa Phe Xaa Xaa Xaa Pro
                125                 130                 135

Ile Xaa Gly Xaa Xaa Ser Xaa Xaa Ala Xaa Xaa Xaa Xaa Leu Ala
                140                 145                 150

Xaa Xaa Xaa Xaa Xaa Lys Tyr Xaa Xaa Phe Xaa Xaa Ala Xaa Leu
                155                 160                 165

Xaa Xaa Xaa Xaa Gln Xaa Xaa Xaa Xaa Xaa Leu Xaa Xaa Xaa
                170                 175                 180

Xaa Xaa Xaa Gly Xaa Xaa Xaa Xaa Xaa Lys Xaa Xaa Xaa Xaa
                185                 190                 195

Xaa Xaa Xaa Ile Xaa Lys Xaa Xaa Xaa Xaa Xaa Xaa Xaa Leu Ala
                200                 205                 210

Gln Xaa Xaa Xaa Xaa Xaa Gly Thr Pro Xaa Xaa Xaa Ile Gly Xaa
                215                 220                 225

Xaa Xaa Xaa Xaa Xaa Xaa Xaa Phe Ile Xaa Gly Ala Xaa Xaa Xaa
                230                 235                 240

Xaa Xaa Leu Xaa Xaa Xaa Ile Asp Xaa Xaa Xaa Xaa
                245                 250
```

```
<210> SEQ ID NO 7
<211> LENGTH: 4
<212> TYPE: PRT
<213> ORGANISM: Ehrlichia spp.
<220> FEATURE:
<223> OTHER INFORMATION: Ehrlichia spp. Conserved cysteine motif
      in active site of thio-disulfide
      oxidoreductase Dsb protein

<400> SEQUENCE: 7

Cys Gly Tyr Cys

<210> SEQ ID NO 8
<211> LENGTH: 4
<212> TYPE: PRT
<213> ORGANISM: Coxiella burnetii
<220> FEATURE:
<223> OTHER INFORMATION: Coxiella burnetii conserved cysteine
      motif in active site of thio-disulfide
      oxidoreductase Com1 protein

<400> SEQUENCE: 8

Cys Gly His Cys

<210> SEQ ID NO 9
<211> LENGTH: 4
<212> TYPE: PRT
<213> ORGANISM: Escherichia coli
<220> FEATURE:
<223> OTHER INFORMATION: Escherichia coli conserved cysteine
      motif in active site of thio-disulfide
      oxidoreductase DsbA protein

<400> SEQUENCE: 9

Cys Pro His Cys

<210> SEQ ID NO 10
<211> LENGTH: 4
<212> TYPE: PRT
<213> ORGANISM: Escherichia coli
<220> FEATURE:
<223> OTHER INFORMATION: Escherichia coli conserved cysteine
      motif in active site of thio-disulfide
      oxidoreductase DsbC protein

<400> SEQUENCE: 10

Cys Gly Tyr Cys

<210> SEQ ID NO 11
<211> LENGTH: 4
<212> TYPE: PRT
<213> ORGANISM: Escherichia coli
<220> FEATURE:
<223> OTHER INFORMATION: Escherichia coli conserved cysteine
      motif in active site of thioredoxin
      protein

<400> SEQUENCE: 11

Cys Gly Pro Cys

<210> SEQ ID NO 12
<211> LENGTH: 21
<212> TYPE: DNA
<213> ORGANISM: Artificial sequence
<220> FEATURE:
<223> OTHER INFORMATION: Forward primer p27nc42 from
      Ehrlichia chaffeensis dsb gene
```

```
<400> SEQUENCE: 12
gagatttcta ctattgactt c                                              21

<210> SEQ ID NO 13
<211> LENGTH: 23
<212> TYPE: DNA
<213> ORGANISM: Artificial sequence
<220> FEATURE:
<223> OTHER INFORMATION: Reverse primer Eca27-700r from
      Ehrlichia canis dsb gene

<400> SEQUENCE: 13
cagctgcacc accgataaat gta                                            23

<210> SEQ ID NO 14
<211> LENGTH: 22
<212> TYPE: DNA
<213> ORGANISM: Artificial sequence
<220> FEATURE:
<223> OTHER INFORMATION: Reverse primer Ecf27-475 from
      Ehrlichia chaffeensis dsb gene

<400> SEQUENCE: 14
ttctaccatg ctgcactaaa cc                                             22

<210> SEQ ID NO 15
<211> LENGTH: 24
<212> TYPE: DNA
<213> ORGANISM: Artificial sequence
<220> FEATURE:
<223> OTHER INFORMATION: Forward primer Ech27f from
      Ehrlichia chaffeensis dsb gene

<400> SEQUENCE: 15
atgctaagga ttttattttt atta                                           24

<210> SEQ ID NO 16
<211> LENGTH: 23
<212> TYPE: DNA
<213> ORGANISM: Artificial sequence
<220> FEATURE:
<223> OTHER INFORMATION: Reverse primer Ech27r from
      Ehrlichia chaffeensis dsb gene

<400> SEQUENCE: 16
tccttgctca tctattttac ttc                                            23

<210> SEQ ID NO 17
<211> LENGTH: 23
<212> TYPE: DNA
<213> ORGANISM: Artificial sequence
<220> FEATURE:
<223> OTHER INFORMATION: Forward primer Ech27-75 from
      Ehrlichia chaffeensis dsb gene

<400> SEQUENCE: 17
atgagcaaat ctggtaaaac tat                                            23

<210> SEQ ID NO 18
<211> LENGTH: 22
<212> TYPE: DNA
<213> ORGANISM: Artificial sequence
<220> FEATURE:
<223> OTHER INFORMATION: Forward primer ECa27-73 from
      Ehrlichia canis dsb gene

<400> SEQUENCE: 18
```

```
atgtctaata aatctggtaa gc                                          22

<210> SEQ ID NO 19
<211> LENGTH: 20
<212> TYPE: DNA
<213> ORGANISM: Artificial sequence
<220> FEATURE:
<223> OTHER INFORMATION: Reverse primer ECa27r from
      Ehrlichia canis dsb gene

<400> SEQUENCE: 19
tttctgcata tctattttac                                             20

<210> SEQ ID NO 20
<211> LENGTH: 4
<212> TYPE: PRT
<213> ORGANISM: Rat
<220> FEATURE:
<223> OTHER INFORMATION: Rat conserved cysteine motif in
      active site of thioredoxin PDI
      protein

<400> SEQUENCE: 20

Cys Gly His Cys
```